United States Patent
Van Eyk et al.

(10) Patent No.: US 6,790,634 B2
(45) Date of Patent: Sep. 14, 2004

(54) METHODS AND COMPOSITIONS RELATING TO PHOSPHORYLATED MYOSIN LIGHT CHAIN 1

(75) Inventors: Jennifer E. Van Eyk, Kingston (CA); David Kent Arrell, Kingston (CA)

(73) Assignee: Queens University at Kingston, Ontario (CA)

( * ) Notice: Subject to any disclaimer, the term of this patent is extended or adjusted under 35 U.S.C. 154(b) by 0 days.

(21) Appl. No.: 09/942,498

(22) Filed: Aug. 30, 2001

(65) Prior Publication Data

US 2003/0044880 A1 Mar. 6, 2003

Related U.S. Application Data

(60) Provisional application No. 60/315,886, filed on Aug. 29, 2001.

(51) Int. Cl.$^7$ .............................. C12Q 1/42; C12N 9/14; A61K 35/34
(52) U.S. Cl. ..................... 435/21; 435/195; 435/372; 424/94.1; 424/569
(58) Field of Search .................. 424/94.1, 569, 424/94; 435/21, 195, 372, 4

(56) References Cited

U.S. PATENT DOCUMENTS 5,906,819 A * 5/1999 Kaibuchi et al.
6,410,254 B1 * 6/2002 Finer et al.

FOREIGN PATENT DOCUMENTS

WO     WO 97/262268    *   7/1997

OTHER PUBLICATIONS

Bialojan et al., "Different Phosphorylation Patterns of Cardiac Myosin Light Chains Using ATP and ATPYS as Substrates", *J. Mol. Cell Cardiol* 1988 20:575–578.

Morano I., "Tuning the human heart molecular motors by myosin light chains", *J. Mol Med* 1999 77:544–555.

Morano et al., "Phosphorylation and Thiophosphorylation by Myosin Light Chain Kinase: Different Effects on Mechanical Properties of Chemically Skinned Ventricular Fibers from the Pig", *J. Mol Cell Cardiol* 1990 22:805–813.

Poetter et al., "Mutations in either the essential or regulatory light chains of myosin are associated with a rare myopathy in human heart and skeletal muscle", *Nature Genetics* 1996 13:63–69.

Rayment et al., "Three–Dimensional Structure of Myosin Subfragment–1: A Molecular Motor", *Science* 1993 261:50–65.

* cited by examiner

*Primary Examiner*—Leon B. Lankford, Jr.
*Assistant Examiner*—Ruth A. Davis
(74) *Attorney, Agent, or Firm*—Licata & Tyrrell P.C.

(57) ABSTRACT

Two novel phosphorylation sites of myosin light chain 1 (MLC1) are described. Methods of monitoring phosphorylation of MLC1 to identify new cardiac and skeletal muscle protective agents, monitor the extent of preconditioning of cardiac and skeletal muscles, and monitoring the status of a subject with cardiac or skeletal muscle damage are provided. Also provided are methods and compositions for altering MLC1 to change contractility of cardiac and skeletal muscles and to protecting cardiac and skeletal muscles from damage caused by conditions and/or agents including, but not limited to, cardiomyopathies, hypertension, free radicals ischemia, hypoxia, and ischemia/hypoxia with reperfusion.

22 Claims, 8 Drawing Sheets

A - Western Blots

Adenosine-treated myocytes

Adenosine, dephosphorylated

Ventricular MLC1 mAb 39-121

B - Composite Images

Adenosine (n=4)

Control (n=4)

METHODS AND COMPOSITIONS RELATING TO PHOSPHORYLATED MYOSIN LIGHT CHAIN 1

INTRODUCTION

This application claims the benefit of priority from U.S. provisional application Serial No. 60/315,886 filed Aug. 29, 2001.

FIELD OF THE INVENTION

The present invention relates to the identification of two novel phosphorylation sites of myosin light chain 1 (MLC1). Phosphorylation of MLC1 at these sites was demonstrated to increase in vivo following pharmacologic preconditioning with adenosine. Monitoring MLC1 phosphorylation provides a useful means for identifying new cardiac or skeletal muscle protective agents, monitoring the extent of preconditioning of cardiac and skeletal muscle tissue, and monitoring the status of a subject with cardiac or skeletal muscle damage. Further, altering MLC1 phosphorylation serves as a means for changing contractility of skeletal and cardiac muscle tissue and for protecting skeletal and cardiac muscle tissue from damage caused by conditions and/or factors including, but not limited to, cardiomyopathies, hypertension, free radicals, ischemia, hypoxia, and ischemia/hypoxia with reperfusion.

BACKGROUND OF THE INVENTION

Ischemic preconditioning (PC), a phenomenon which exists in all species examined, including humans(Cohen, M. V. and Downey, J. M. Lancet 1993 342:6; Yellon et al. Lancet 1993 342:276–277; Kloner et al. J. Am. Coll. Cardiol. 1994 24:1133–1142), is a form of protection whereby a brief ischemic episode reduces the extent of damage to cardiac and/or skeletal muscle tissue from subsequent prolonged ischemia (Murry et al. Circ. 1986 74:1124–1136). PC may also be recruited pharmacologically, with one of many activators being adenosine, a by-product of adenosine triphosphate (ATP) metabolism (Liu et al. Circ. 1991;84:350–356). Both ischemic and pharmacological PC trigger two windows of protection, the first (classical PC) becoming manifest within 15 minutes and lasting 1–3 hours (Cohen, M. V. and Downey, J. M. Lancet 1993 342:6; Van Winkle et al. Cor. Art Dis. 1991 2:613–619; Li et al. Am. Heart J. 1992 123:346–353; Lawson et al. J. Mol. Cell Cardiol. 1993 25:1391–1402). The short duration of protection afforded by classical PC is likely the result of post-translational protein modifications, as 15 minutes does not suffice to recruit de novo transcription and translation. In contrast, the second window (late or delayed PC), which is manifested 24–72 hours after the conditioning stimulus (Marber et al. Circ. 1993 88:1264–1272; Kuzuya et al. Circ. Res. 1993 72:1293–1299) involves changes in gene expression (Bolli R. Circ Res. 2000 87:972–983) as well as post-translational protein modifications.

While the protective effect of PC is well established, the molecular mechanisms of PC remain elusive. Current research into classical PC focuses primarily on the opening of the inner mitochondrial ATP-sensitive potassium (mitoK$_{ATP}$) channel in response to activation of complex kinase signaling cascades (Cohen et al. Annu. Rev. Physiol. 2000 62:79–109; Marber, M. S. Circ. Res. 2000 86:926–931). Ischemia-induced release of adenosine, bradykinin, opioids, and free radicals leads to receptor-mediated activation of protein kinase C (PKC) (Cohen et al. Annu. Rev. Physiol. 2000 62:79–109; Marber, M. S. Circ Res. 2000 86:926–931). Kinases downstream from PKC that have been implicated in PC include a tyrosine kinase, and a number of mitogen-activated protein kinases (MAPKs), the most likely candidates of which are in the c-Jun N-terminal kinase (JNK) and p38 MAPK families (Cohen et al. Annu. Rev. Physiol. 2000 62:79–109). A key downstream effect of this cascade appears to be the opening of mitoK$_{ATP}$ channels, as pharmacological channel opening mimics genuine ischemic PC, and mitoK$_{ATP}$ channel blockers abolish cardioprotection (Grover, G. J. J. Cardiovasc. Pharmacol. 1994 24:S18–S27). The metabolic protective effects of channel opening may result from a reduction in ATP hydrolysis (Garlid et al. Circ Res. 1997 81:1072–1082) and an influx of $Ca^{2+}$ into the mitochondria (Holmuhamedov et al. FASEB J. 1999 13:A1079(Abstr)). PC has also been demonstrated to protect against functional myofilament changes of stunned myocardium in rat trabeculae (Perez et al. Cardiovasc. Res. 1999 42:636–643), thus implying that modification to myofilament proteins may also potentiate protection.

SUMMARY OF THE INVENTION

An object of the present invention is to provide methods for identifying agents which protect cardiac, skeletal and smooth muscles from damage via their ability to increase MLC1 phosphorylation in the muscle tissue.

Another object of the present invention is to provide methods and compositions for protecting cardiac and skeletal muscles from damage by increasing phosphorylation of MLC1 in the muscle tissue.

Another object of the present invention is to provide methods and compositions for altering the contractility of cardiac and skeletal muscles by modulating MLC1 phosphorylation in the muscle tissue.

Another object of the present invention is to provide methods for monitoring the phosphorylation status of MLC1 in a subject. Such methods are useful in evaluating whether or not a subject is adequately protected from damage to cardiac and skeletal muscles caused by conditions and/or factors such as cardiomyopathies, hypertension, free radicals, ischemia, hypoxia, and ischemia/hypoxia with reperfusion. In addition, the status of MLC1 phosphorylation is useful in assessing the status of myocardial damage in a subject.

Yet another object of the present invention is to provide methods for identifying kinases and/or phosphatases that act on MLC1 as therapeutic targets for agents that modulate or protect against damage to cardiac and skeletal muscles.

BRIEF DESCRIPTION OF THE FIGURES

FIG. 2A shows a silver stained 2-DE gel of the whole cell homogenate within a pH range of 3.0 to 10.0. FIG. 2B shows a silver stained 2-DE gel of the first extract (proteins soluble at pH 7.4) containing the cytosolic fraction within a pH range of 3.0 to 10.0. FIG. 2C shows a silver stained 2-DE gel of the second extract (protein soluble at pH 2.0) which is enriched for myofilament protein within a pH range of 4.0 to 7.0.

Enlargements of Regions 1 and 2 from 2-DE gels of adenosine-treated (Ado) and control (Ctrl) myocytes are shown in the side panels for comparison. The positions of SDS-PAGE molecular weight standards are indicated on the left of the 2-DE gel.

Figure 4:
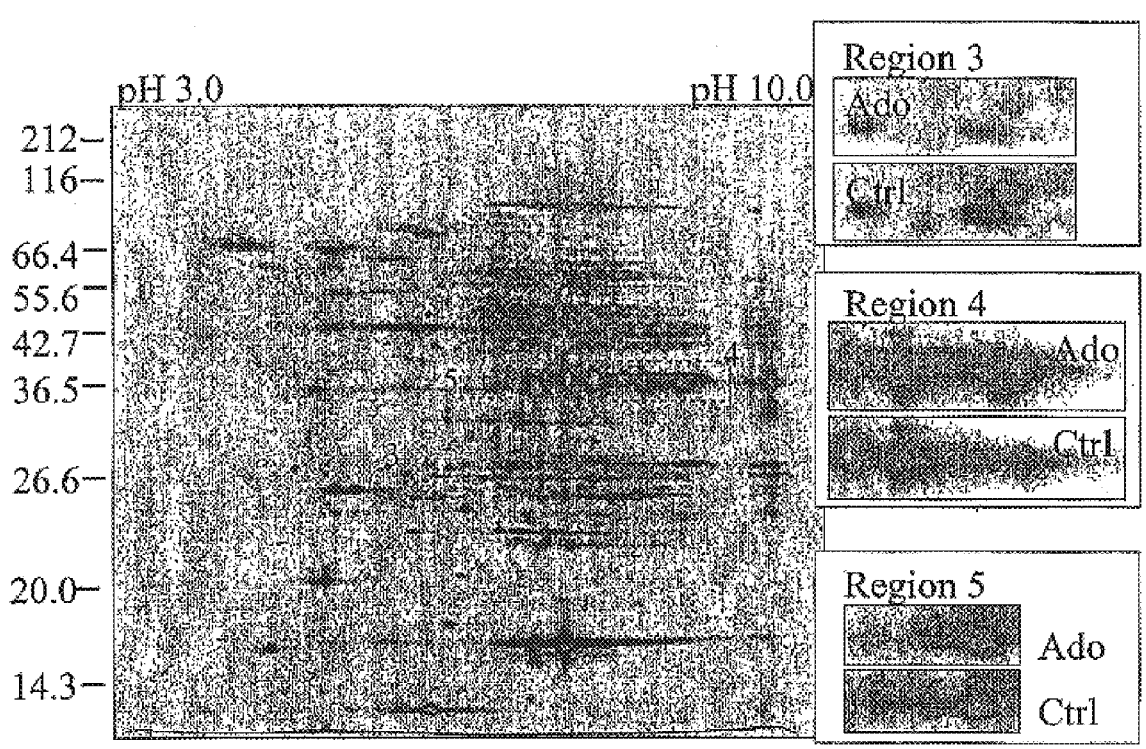

FIG. 4 shows adenosine-induced changes to a rabbit ventricular myocyte cytosolic subproteome. Cytosolic subproteomes obtained by "IN Sequence" sequential extraction at pH 7.4 were separated by 2-DE to identify adenosine-induced protein modifications. The large panel (pH 3–10 linear gradient) shows a silver-stained gel of adenosine-treated cytosolic extract (90% of the protein extracted from 750 μg of whole-cell homogenate). Adenosine-induced protein modifications observed in these extracts are indicated by dashed boxes, designated 3 (~28 kDa, pI~5.5), 4 (~37 kDa, pI ~8.5), and 5 (~36 kDa, pI~6.0). Enlargements of these regions from 2-DE gels of adenosine-treated (Ado) and control (Ctrl) samples are shown in the side panels for comparison. The positions of SDS-PAGE molecular weight standards are indicated on the left of the 2-DE gel.

Figure 5:
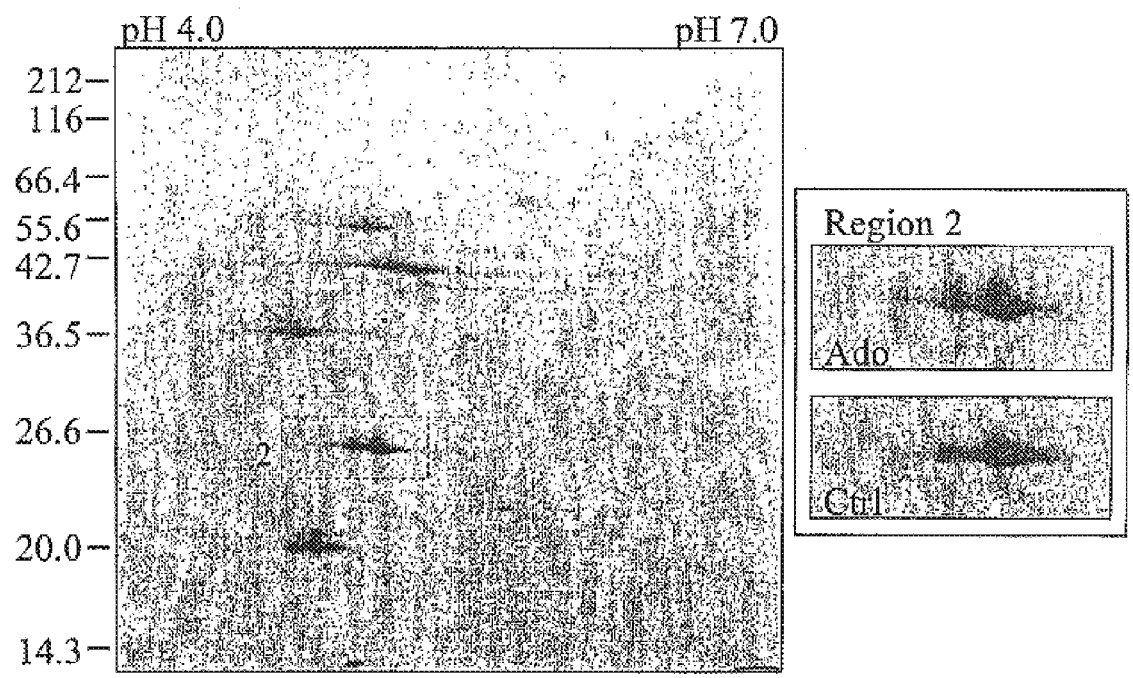

FIG. 5 shows adenosine-induced changes to a rabbit ventricular myocyte myofilament-enriched subproteome. Myofilament-enriched subproteomes obtained by "IN Sequence" sequential extraction at pH 2.0 were separated by 2-DE to identify adenosine-induced protein modifications. The large panel (pH 4–7 linear gradient) shows a silver-stained gel of adenosine-treated myofilament-enriched extract (containing 10% trifluoroacetic acid (TFA)-solubilized protein isolated from cytosolic extract pellets from the extraction shown in FIG. 4). An adenosine-induced protein modification observed in these extracts is indicated by a dashed box, designated 2, as it corresponds to Region 2 indicated in FIG. 3 (~26 kDa, pI ~4.7–5.0). Enlargement of this region from 2-DE gels of adenosine-treated (Ado) and control (Ctrl) samples is shown in the side panel for comparison. The positions of SDS-PAGE molecular weight standards are indicated on the left of the 2-DE gel.

Figure 6:
Figure 6:
Figure 6:
Figure 6:

FIG. 6 shows MLC1 phosphorylation and adenosine-induced modulation in rabbit ventricular myocytes. Western blots of 2-DE resolved rabbit ventricular myocyte whole-cell homogenates probed with an anti-ventricular MLC1 mAb (pH 4–7) are shown in panel A. Prior to 2-DE, a single aliquot of adenosine-treated myocytes was divided into two equal portions, with one aliquot subjected to alkaline phosphatase dephosphorylation (lower panel) for comparison to the adenosine-treated myocytes (upper panel). Panel B shows the position of MLC1 (Region 2) from composite images of myofilament-enriched extracts of adenosine-treated (upper panel) and control myocytes (lower panel), illustrating the difference in the amount of mono-phosphorylated MLC1.

Figure 7:
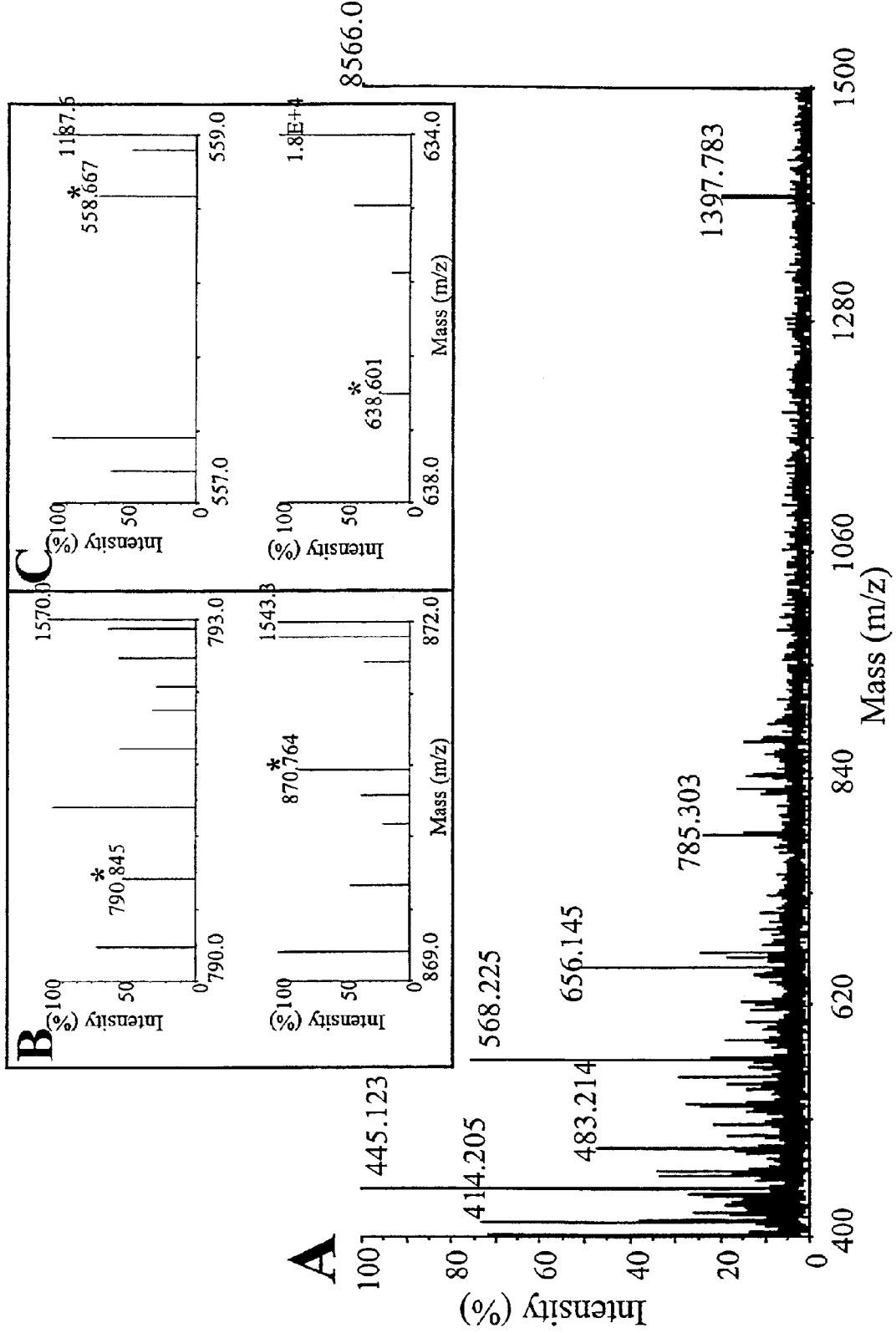

FIG. 7 shows mass spectrometry of MLC1. Identification of MLC1 by tryptic peptide mass fingerprinting was carried out as outlined in the methods section. A typical MLC1 spectrum of mass peaks obtained between 400 and 1500 Da is shown in panel A. Two tryptic peptide fragments, with masses of 790.845 (panel B, top) and 558.667 Da (panel C, top), present in spectra obtained from unphosphorylated MLC1 spots were reduced markedly in spectra from mono-phosphorylated MLC1 spots. Instead, two additional fragments were detected, with masses of 870.764 (panel B, bottom) and 638.601 Da (panel C, bottom). The 80 Da shifts correspond to the addition of a phosphate moiety. Peptide mass fingerprinting and sequence alignments matched the altered fragments to theoretical tryptic digests of rat and human ventricular MLC1. Sequence analysis matched these phosphorylated peptide fragments with rat and human fragments containing phosphorylatable residues, corresponding to Thr69 and Ser200 for rat (Thr64 and Ser194 or 195 for human MLC1).

Figure 8:
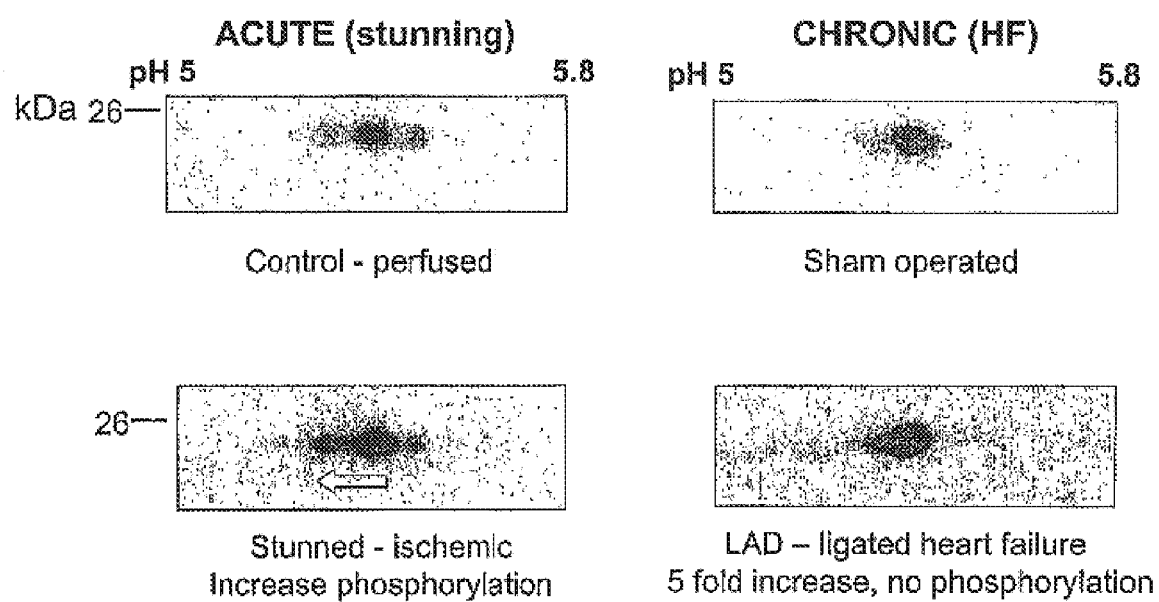

FIG. 8 provides western blots of a MLC1 2-DE gel in an in vivo swine model following acute injury (stunning) and chronic injury (heart failure, HF) to the myocardium.

DETAILED DESCRIPTION OF THE INVENTION

All cited patents, patent applications, and publications are incorporated herein by reference in their entirety. Proteomics is a method of observing, concomitantly, changes to the entire protein complement (proteome) of a particular tissue or organ. Proteomic analyses are routinely carried out by methods of protein separation, such as two-dimensional gel electrophoresis (2-DE) or high performance liquid chromatography (HPLC), followed by methods of protein identification and characterization, including immunodetection and mass spectrometry. 2-DE is a powerful technique for resolving hundreds to thousands of proteins at one time, while simultaneously enabling the resolution of a single protein into its various post-translationally modified forms. This facilitates identification of subtle protein changes, which may be associated with a particular condition or disease state. However, while 2-DE gels separate hundreds to thousands of proteins, differences in charge, hydrophobicity, and protein copy number (abundance) make it impractical to inspect an entire proteome within a single gel.

A subproteomic approach, whereby proteins are analyzed after fractionation by specific characteristics (i.e. charge, solubility, intracellular location), facilitates investigation of highly complex proteomes (Cordwell et al. Electrophoresis 2000 21:1094–1103).

In the present invention, an extraction method, referred to herein as the "IN Sequence" extraction method was used to reduce proteome complexity and isolate a single extract enriching for many myofilament proteins. The myofilament proteins are the most highly abundant proteins in muscle cells, making "IN Sequence" particularly useful for proteomic studies of muscle. Not only do the myofilament proteins fractionate together, but the fact that they do facilitates not only their investigation, but also that of numerous lower abundance proteins. For example, loading may be increased in myofilament-free extracts to study lower abundance proteins, without interference by these highly abundant myofilament proteins. Furthermore, reduction of proteome complexity enables detection and quantification of very subtle post-translational protein modifications, such as that observed with increased MLC1 phosphorylation by adenosine-induced preconditioning. Quantification of such changes would otherwise be severely limited, if not impossible, due to the contribution of other co-migrating proteins present in the whole cell proteome.

Using proteomic analysis, protein modifications involved in triggering classical pharmacological preconditioning (PC) were investigated. A novel phosphorylation of ventricular myosin light chain 1 (MLC1), also referred to as essential light chain (ELC) and DTNB (5,5'-dithiobis-(2-nitrobenzoic acid) light chain, the extent of which increased significantly upon adenosine-induced PC, was identified. Insofar as $LC_{17}$, the essential light chain (ELC) of smooth muscle, is expected to have one or more phosphorylatable sites, the invention is also applicable to smooth muscle.

Figure 2:
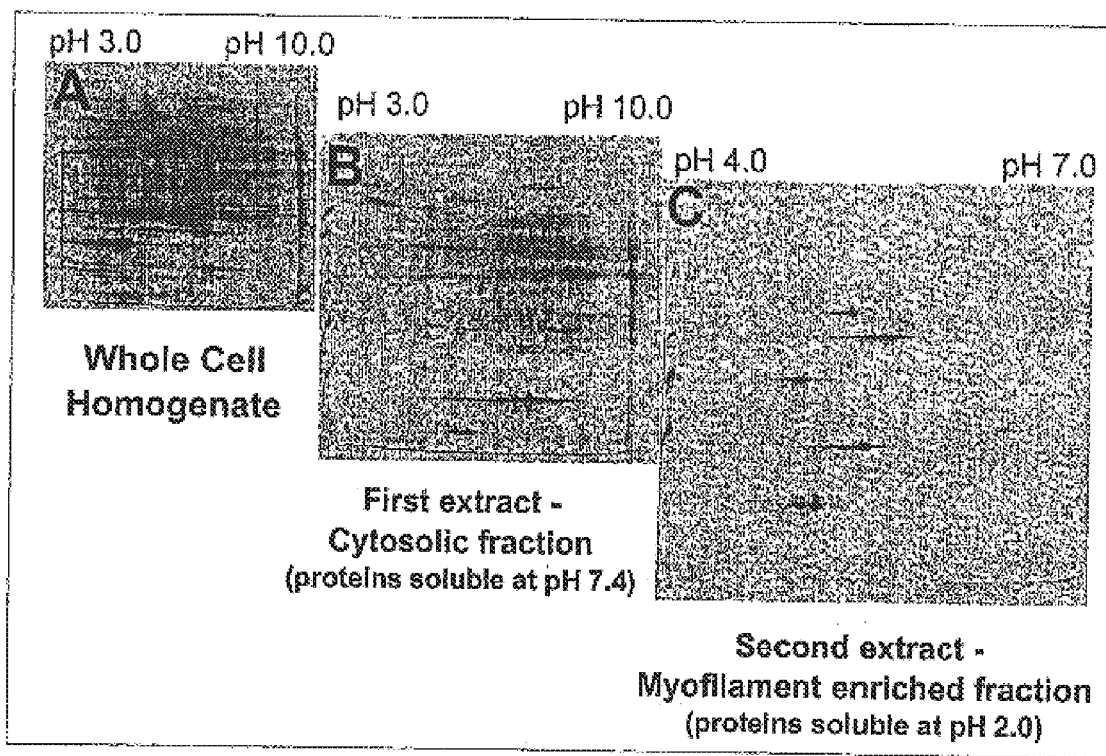
FIG. 2 shows silver stained 2-DE gels of rabbit ventricular myocyte proteins subjected to the "IN Sequence" protein extractions described in Example 2.

In these experiments, proteins from isolated rabbit ventricular myocytes were first resolved by two-dimensional gel electrophoresis and then detected by silver staining. The silver stained 2-DE gels of rabbit ventricular myocyte proteins, resolved in a linear pH range of 3–10, revealed roughly 1500 protein spots at greatly varying abundances. At lower protein loads, adenosine-induced protein changes were evident in silver-stained 2-DE gels of whole cell homogenates. To facilitate protein modification analysis, sequential subproteomes were isolated using the "IN Sequence" extraction protocol as described in Example 2. Numerous low abundance proteins were enriched following the initial extractions at physiological pH, enabling visualization of protein changes not evident in whole cell homogenates. Approximately 800 protein spots were detected in these extracts. Subsequent acid extraction greatly enriched many of the high abundance myofilament proteins. As the pI of most of these proteins is close to pH 5, their resolution was improved by separation with a narrower pH gradient of 4–7, yielding 55 detectable protein spots (see FIG. 2).

Using the BioImage software INVESTIGATOR™ HT Proteome Analyzer 1.0.1 (Genomic Solutions, Inc.) composite images of protein spots were prepared from individual silver-stained 2-DE gels for four sets of paired adenosine-treated and untreated cardiomyocytes obtained from different rabbit hearts. All spots were quantified and matched, then normalized by a match ratio method using 2-DE gels at optimal staining levels. Accurate quantification of protein spots was possible only when it was determined that the spot intensity was within a linear range of concentration for silver staining, and therefore neither saturated nor under represented.

Figure 3:
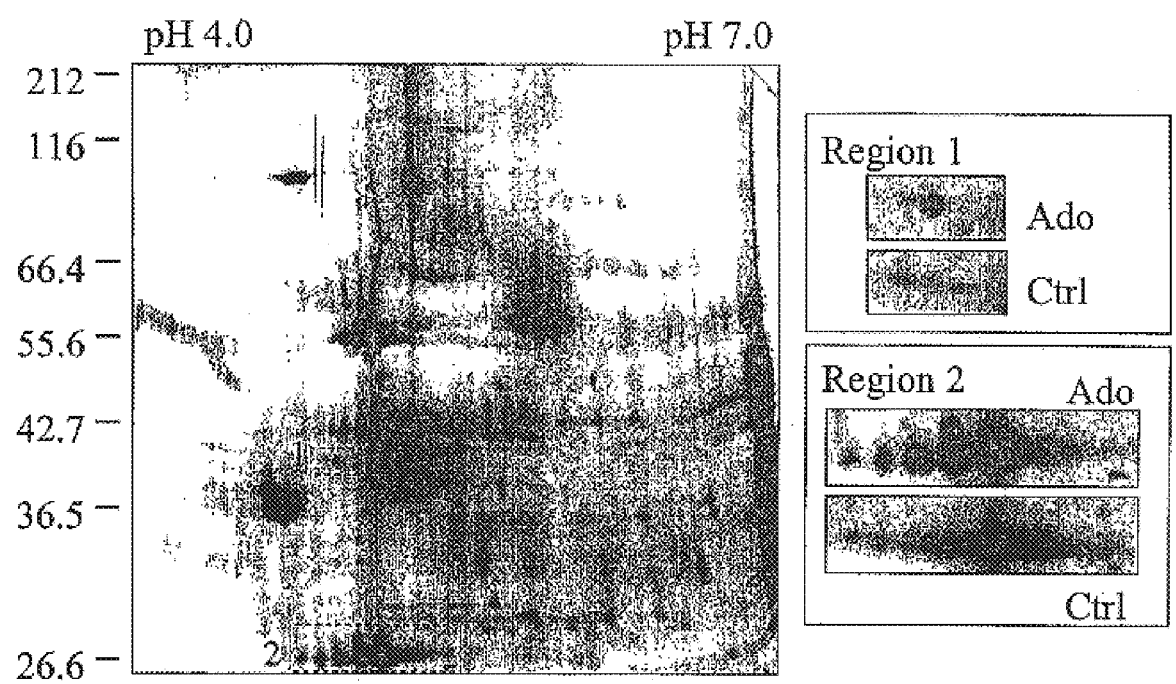
FIG. 3 shows examples of adenosine-induced modifications to the rabbit ventricular myocyte proteome. Whole cell homogenates of rabbit ventricular myocyte proteins were separated by 2-DE to identify adenosine-induced protein modifications. Shown is a representative silver-stained 2-DE gel of adenosine-treated myocytes at a protein load of 250 μg (pH 4–7). Positions of adenosine-induced protein modifications observed are indicated by dashed boxes, designated 1 (~40 kDa, pI~4.8) and 2 (~26 kDa, pI~4.6–5.0).

Comparison of adenosine and control composite images revealed that myofilament-enriched acid extracts possessed a highly reproducible difference for a series of three spots with a relative migration ($M_r$) of ~26 kiloDaltons (kDa) and an isoelectric point (pI) range of ~4.7–5.0 (See FIGS. 3 to 5). Based on relative protein abundance, pI, $M_r$, and comparison to known ventricular protein 2-DE gel databases, these spots were suspected to be myosin light chain 1 (MLC1). This was confirmed by western blotting of 2-DE separated whole cell homogenates with an antibody specific for MLC1, which showed a three spot alignment identical to those observed for both the composite image and the silver stained gels (see FIG. 6). Dephosphorylation of protein from adenosine-treated myocytes prior to 2-DE separation revealed that MLC1 was phosphorylated, as the three spot pattern collapsed to a single spot, corresponding to the most basic of the three original protein spots. Thus, MLC1 was present in rabbit ventricular myocytes as a mixed population of un-, mono-, and di-phosphorylated protein. To ensure that MLC1 modification was not an artifact occurring during the experimental protocols, the "IN Sequence" extraction and 2-DE separation of proteins extracted directly from intact rabbit ventricular tissue were repeated and the same three spot pattern for MLC1 was observed by both silver staining and immunoblotting.

The percentages of the various MLC1 forms were quantified from the silver stained 2-DE gels under optimal staining conditions for MLC1 in all gels, such that all three MLC1 spots were neither under nor over represented. MLC1 phosphorylation increased from 25.7±1.6% (mean ± standard error) in drug-free controls, to 34.0±2.7% following treatment with adenosine. This change in MLC1 phosphorylation was found to be statistically significant (P<0.05) by one way ANOVA.

Mass spectrometry was then performed on protein isolated from silver stained 2-DE gels (see FIG. 7). Analysis of trypsin-digested protein fragments isolated from each of the three spots resulted in highly consistent mass spectra. Two variations were identified between spectra obtained from unphosphorylated and phosphorylated MLC1 spots, indicating differences in the peptide fragments present. Fragments with masses of 558.667 and 790.845 Da were present in unphosphorylated MLC1 spectra, but were conspicuously absent from phosphorylated samples. Instead, the spectra obtained from the phosphorylated MLC1 samples contained two other fragments that were not present in unphosphorylated samples, with masses of 638.601 and 870.764 Da. Addition of a phosphate moiety (79.9797 Da) to each of the two unique fragments in the upper spectra resulted in phosphopeptides varying in mass by less than 0.1 Da from the two unique fragments in the lower spectra.

Peptide mass fingerprinting matched theoretical tryptic peptide fragments derived from rat ventricular MLC1 sequence (GenBank Accession No. P16409) to both the 638.601 and 870.764 Da phosphopeptides of rabbit MLC1. Rat MLC1 amino acids (a.a.) 196–200 matched the smaller phosphopeptide fragment, while a.a. 69–75 matched the larger phosphopeptide fragment. Using Clustal W (version 1.81), these peptides were found to align with human ventricular MLC1 (GenBank Accession No. P08590) a.a. peptide fragments 64–70 and 191–195, respectively. Each of the identified fragments contains a potential phosphorylation site, at Thr69 and Ser200 for rat MLC1, and at Thr64 and Ser194 or Ser195 for human MLC1. Clustal W sequence alignments also revealed that these two regions of MLC1 were highly conserved among species and across muscle types. The same pattern of phosphorylation of MLC1 has been observed not only in humans, but also in rats, dogs and swine.

As discussed above and in the below examples, phosphorylation of MLC1 after a 60 minute exposure of cells to adenosine was about 34%. However, adenosine exposure results in a rapid second messenger response. Therefore, a larger increase in MLC1 phosphorylation is expected to occur within the first 60 minutes period of adenosine exposure (e.g., within the first 5 to 10 minutes), with a subsequent decline to the steady-state value in a normal healthy subject of about 25% thereafter. The 34% phosphorylation discussed herein is likely a value along the decline to steady-state. This can be confirmed by monitoring the extent of MLC1 phosphorylation over a 60 minute period to produce a time course of phosphorylation. The provision of a such time course will enhance therapeutic and diagnostic aspects of the invention, as, for example, it will allow the extent of damage to be more accurately assessed.

Figure 1:
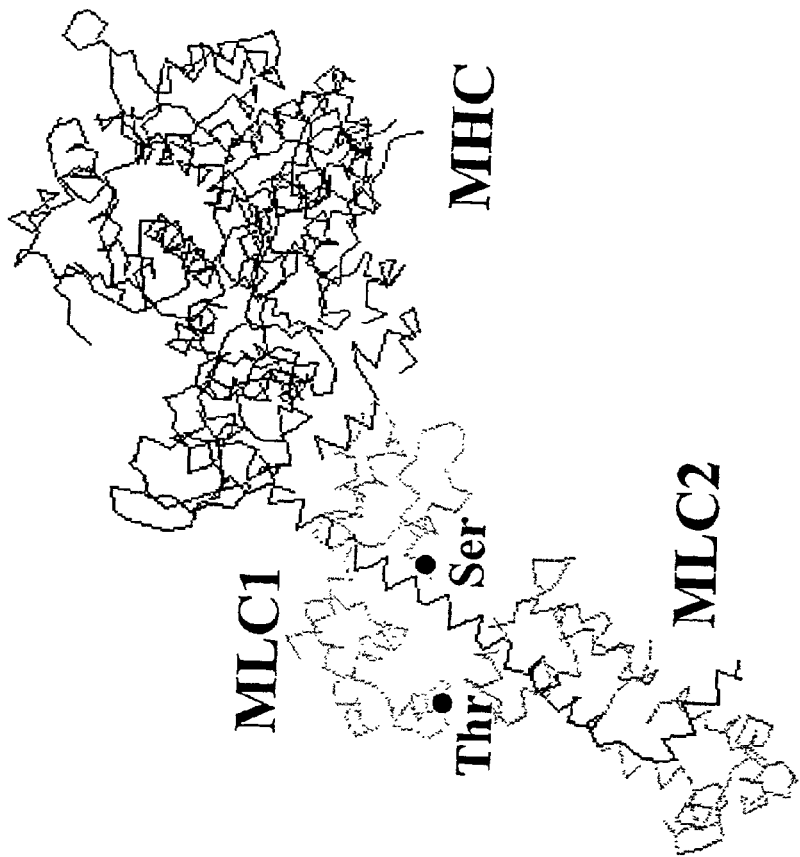
FIG. 1 provides a model of the structure of the S1 portion of myosin including myosin light chain 1 (MLC1), myosin light chain 2 (MLC2) and the myosin heavy chain globular head and lever regions. The phosphorylation sites are highlighted.

The present invention provides the first demonstration of in vivo MLC1 phosphorylation via the identification of these two novel phosphorylation sites. Based on the highly conserved sequence of MLC1 and the crystal structure of the myosin head region (Rayment et al. Science 1993 261:50–8), it is believed that both phosphorylation sites reside in exposed regions of the protein near the myosin heavy chain (MHC) lever arm. The serine site is located directly adjacent to the MHC lever arm extending through MLC1, while the threonine site is located in the region of closest proximity between MLC1 and MLC2, a protein which is also associated with the MHC lever arm adjacent to MLC1 (see FIG. 1). The fact that the level of phosphorylation increased significantly upon adenosine-induced PC is indicative of MLC1 phosphorylation serving as a protective end effector of adenosine preconditioning.

Accordingly, one aspect of the present invention relates to methods for identifying agents protective against cardiac and skeletal muscle damage by the ability of the agent to increase MLC1 phosphorylation. Agents identified as increasing MLC1 phosphorlyation inhibit damage to cardiac and skeletal muscles caused by conditions and/or factors including, but not limited to, cardiomyopathies, hypertension, free radicals, ischemia, hypoxia, and ischemia/hypoxia with reperfusion. These agents are also referred to herein as muscle protective agents. Such agents are useful in protecting muscle in, for example, surgical procedures, heart transplant, and heart harvesting.

The ability of a potential muscle protective agent to increase MLC1 phosphorylation can be assessed in vitro in purified cardiac or skeletal myosin, myosin light chain 1, or isoforms thereof, or in myofilament or skinned muscle fibers. In one embodiment, adenosine triphosphate (ATP) and the potential protective agent are added to the purified myosin, myosin light chain 1 or isoform thereof, or the myofilament or skinned muscle fiber and the phosphorylation of MLC1 is monitored. MLC1 phosphorylation can be detected by various methods including, but not limited to, 2-DE using either a general or specific anti-MLC1 antibody, silver staining or $^{32}P$ labeling, and 1-DE using either $^{32}P$ or anti-phospho-specific antibody. For example, monitoring after heart surgery or transplant provides information about the status of a patient's recovery.

The ability of a potential muscle protective agent to increase MLC1 phosphorylation can also be assessed in isolated myocytes or whole hearts either isolated using Langendorff apparatus or in vivo. In these embodiments, the ability of a potential muscle protective agent to trigger preconditioning can be assessed by monitoring MLC1 phosphorylation status. MLC1 phosphorylation in these embodiments can also be detected by methods such as 2-DE using either an anti-MLC1 antibody, silver staining or $^{32}P$ labeling, or 1-DE using either $^{32}P$ or anti-phospho-specific antibody.

The ability of a potential muscle protective agent to increase MLC1 phosphorylation can then be confirmed in vivo by administering the agent to a subject and monitoring the level of MLC1 phosphorylation in a biological sample of the subject. For purposes of the present invention, by "biological sample" it is meant to include, but is not limited to, biological fluids such as serum, plasma, urine, milk, lymph, amniotic fluid, semen and cerebrospinal fluid, and biological tissues, such as cardiac, skeletal, and smooth muscle. In a preferred embodiment, the biological sample is serum.

In all of these embodiments, it is preferred that MLC1 phosphorylation levels be determined in the presence and absence of the potential muscle protective agent. An increase in the MLC1 phosphorylation levels in the presence of the agent as compared to the MLC1 phosphorylation levels in the absence of the agent is indicative of the agent being protective of the myocardium against damage caused by conditions and/or factors including, but not limited to, cardiomyopathies, hypertension, free radicals, ischemia, hypoxia, and ischemia/hypoxia with reperfusion.

Agents identified as protective may be administered as pharmaceutical compositions to a subject in need of a muscle protective agent. Methods for formulating these agents with a biocompatible carrier to produce a pharmaceutical composition are well known and taught in standard reference text books such as *Pharmaceutical Dosage Forms* (Lieberman, Rieger and Banker (Eds.), 1988, Marcel Dekker, Inc., New York, N.Y.) and *Remington's Pharmaceutical Sciences*, Mack Publishing Co., Easton, Pa., 1985. Thus, pharmaceutical formulations comprising muscle protective agents identified in accordance with the teachings provided herein and a biocompatible carrier can be prepared routinely by those of skill in the art. These agents can also be incorporated into cardioplegia solutions (e.g. cardioplegia solution Catalog No. 2B1462 from Baxter Healthcare Corp.) used during heart surgery and to transport donor hearts for transplantation. It is preferred that the muscle protective agent of the compositions and cardioplegia solutions not be adenosine.

Accordingly, the present invention also relates to methods and compositions for protecting the cardiac and skeletal muscle from damage by increasing phosphorylation of MLC1 in the muscle. Compositions comprising an agent which increases phosphorylation of MLC1 and a biocompatible carrier can be administered to a subject in need thereof to protect muscle from damage resulting from or caused by conditions and/or agents including, but not limited to, cardiomyopathies, hypertension, free radicals ischemia, hypoxia, and ischemia/hypoxia with reperfusion. For example, in one embodiment an agent identified as increasing MLC1 phosphorylation can be administered to a subject prior to a surgical procedure wherein it is suspected that cardiac or skeletal muscles will be exposed to ischemic and/or hypoxic conditions. Examples of such procedures include, but are not limited to, coronary artery bypass surgery, heart transplants, angioplasty, and valve replacements. Agents identified as increasing MLC1 phosphorylation can also be administered to subjects exhibiting chest pain as a means of decreasing injury to the heart resulting from a potential infarction. Such agents can also be administered to a subject prior to administration of a chemotherapeutic agent such as radiation therapy known or suspected to cause damage to the skeletal and/or cardiac muscles.

Administration of agents which modulate MLC1 phosphorylation also alter contractility of cardiac and skeletal muscles. Accordingly, the present invention also relates to methods and compositions for altering contractility of cardiac and skeletal muscles by contacting the muscle with an agent which modulates MLC1 phosphorylation status. By the term "modulate", "modulating" or "modulation" as used herein, it is meant either an increase in MLC1 phosphorylation or a decrease in MLC1 phosphorylation. Such methods and compositions are useful in increasing muscle function following a surgical procedure wherein the muscle was stunned or in conditions such as heart failure wherein the muscle is weakened and cannot maintain its required output.

The present invention also relates to methods of monitoring the phosphorylation status of MLC1 in a subject to evaluate whether or not cardiac and skeletal muscles are protected from damage resulting from conditions and/or factors including, but not limited to, cardiomyopathies, hypertension, free radicals, ischemia, hypoxia, and ischemia/hypoxia with reperfusion. This method is useful in assessing the level of protection of cardiac and skeletal muscles in a subject prior to and following a surgical procedure, particularly heart surgery, as well prior to administration of a chemotherapeutic agent such as radiation therapy which may result in damage to the muscle tissue.

In addition, monitoring the phosphorylation status of MLC1 provides a means for assessing the status of cardiac and/or skeletal muscle damage in a subject. For example, MLC1 has been shown to be phosphorylated in acute injuries of the myocardium such as preconditioning and early stages of ischemic injury (see FIG. 8). However, phosphorylated MLC1 was not observed in the myocardium in chronic conditions such as heart failure (see FIG. 8). In fact, levels of phosphorylated MLC1 in this heart failure model were equal to or less than basal levels measured in control animals. Accordingly, the phosphorylation status of MLC1 is believed to be useful in distinguishing early damage to the myocardium from more severe, longer term damage. Further, it is believed that administration of a muscle protective agent which increases MLC1 phosphorylation can be used to raise levels of MLC1 phosphorylation in subjects suffering from chronic heart failure, thereby alleviating further damage to the heart and increasing heart function.

The identification of MLC1 phosphorylation sites also facilitates identification of kinases and/or phosphatases that act on MLC1, and in particular MLC1 phosphorylation. The identification of such kinases and/or phosphatases will be useful in identifying new therapeutic targets for agents which modulate MLC1 phosphorylation status.

The following nonlimiting examples are provided to further illustrate the present invention.

EXAMPLES

Example 1

Isolation and Preconditioning of Rabbit Ventricular Myocytes

Rabbits were used in compliance with the Animals for Research Act (Province of Ontario), the Canadian Council on Animal Care, and the *Guide for the Care and Use of Laboratory Animals* published by the US National Institutes of Health (NIH publication No. 85–23, revised 1985).

Rabbit ventricular myocytes were isolated by collagenase dissociation in accordance with procedures described by Liu et al. (Circ. Res. 1996 78:443–454). In this procedure, hearts were excised from anesthetized (30 mg/kg pentobarbital IV) New Zealand White rabbits (weighing 1 to 2 kg) and mounted on a Langendorff apparatus. The heart was subjected to retrograde perfusion with modified Krebs-Henseleit solution composed of (in mmol/L) NaCl 119, KCl 5, $NaHCO_3$ 25, $KH_2PO_4$ 1, $MgSO_4$ 1, $CaCl_2$ 2, and glucose 10, with 95% $O_2$/5% $CO_2$ at 37° C. Hearts were equilibrated for five minutes, perfused without $Ca^{2+}$ for five minutes, then with perfusate containing collagenase (1.0 mg/mL, Worthington type II) for fourteen minutes. The perfusion pressure was monitored, and the flow rate was adjusted to maintain perfusion pressure at ≈75 mm Hg. Ventricles were minced and cells were filtered through nylon mesh and washed several times with a high-$K^+$ solution consisting of (in mmol/L) potassium glutamate 120, KCl 25, $MgCl_2$ 1, N-2-hydroxyethyl piperazine-N-2-ethanesulfonic acid (HEPES) 10, EGTA 0.1, and glucose 10. Cells were then washed in a modified Tyrode's solution containing (in mmol/L) NaCl 140, KCl 5, $CaCl_2$ 1, $MgCl_2$ 1, and HEPES 10 (pH 7.4), yielding >50% of $Ca^{2+}$-tolerant ventricular myocytes.

Cell isolation was followed directly by pharmacological preconditioning, which was carried out by treatment with 100 μmol/L adenosine (Sigma) for 60 minutes in a 37° C. water bath in accordance with the procedure described by Sato et al. (Circ. 2000 102:800–805). Untreated cells were prepared concurrently as controls. Equivalent 25 μL aliquots of cells (containing ~30 mg/mL of protein as determined by Lowry assay (Lowry et al. J. Biol. Chem. 1951 193:265–275)) were frozen in a dry ice/ethanol bath, and stored at −80° C. until analysis.

Example 2

"IN Sequence" Protein Extraction and Protein Dephosphorylation

Every step in the "IN Sequence" protein extraction protocol was carried out on ice or at 4° C., and all centrifugations were conducted at 4° C. for 2 minutes at 16000×g. Aliquots (25 μL) of myocytes were mechanically homogenized in 100 μL of HEPES extraction buffer, consisting of (in mmol/L) HEPES 25 (pH 7.4), NaF 50, $Na_3VO_4$ 0.25, phenylmethylsulfonyl fluoride 0.25, EDTA 0.5, and (in μmol/L) leupeptin 1.25, pepstatin A 1.25. The homogenate was centrifuged, and the supernatant removed and saved. A second HEPES extraction was performed on the pellet and pooled with the supernatant from the first extraction. The remaining pellet was subjected to further extraction by mechanical homogenization in 50 μL of acid extraction buffer, consisting of 1% v/v trifluoroacetic acid (TFA) and 1 mmol/L Tris (2-carboxyethylphosphine) hydrochloride (pH~2.0). Again, the homogenate was centrifuged, and the supernatant removed and saved. An additional TFA extraction was performed on the pellet and pooled with supernatant from the previous TFA extraction. The supernatants and remaining pellet were then frozen and stored at −80° C. HEPES extractions (extracts 1 and 2) enrich for soluble cytosolic proteins, while TFA extractions (extracts 3 and 4) enrich for many myofilament proteins.

Proteins were dephosphorylated using the following protocol. Essentially, 25 μL aliquots of myocytes were mechanically homogenized to lyse cells, then divided into two equal volumes (~375 μg protein each). A total of 2.5 μL of 10× alkaline phosphatase reaction buffer was added to each sample, consisting of (in mmol/L) NaCl 1000, $MgCl_2$ 100, dithiothreitol (DTT) 10, Tris-HCl 500 (pH 7.9 at 25° C.). To one sample, a 10 μL aliquot of calf intestinal alkaline phosphatase (10 units/μL, New England Biolabs) in 50% glycerol and (in mmol/L) KCl 50, $MgCl_2$ 1, $ZnCl_2$ 0.1, Tris-HCl 10 (pH 8.2) was added, while 10 μL of the same solution lacking alkaline phosphatase was added to the control. Samples were incubated at 37° C. for 15 minutes and the reaction stopped by addition of 20 volumes (500 μL) of isoelectric focusing (IEF) buffer (8 mol/L urea, 2% w/v 3-[3-cholamidopropyl]-1-propane-sulfonate, 0.5% pH 4.0–6.5 ampholytes, 50 mM DTT, and 0.01% w/v bromophenol blue).

Example 3

Isoelectric Focusing (IEF)

IEF was carried out using a PROTEAN® IEF cell (Bio-Rad) essentially according to the manufacturer's protocol. Protein samples were initially dissolved in 500 μL of IEF buffer, loaded into the focusing tray, overlaid with 170 mm pH 4–7 immobilized linear pH gradient READY STRIPS™ (Bio-Rad), then covered with mineral oil. Gels were actively rehydrated at 50 volts (V) for 10 hours to enhance protein uptake, then subjected to the following conditions using a rapid voltage ramping method limited by a maximum current of 50 μA per gel: 100 V for 25 Volt-hours (Vh), 500 V for 125 Vh, 1000 V for 250 Vh, and 8000 V for 85 kVh. A Peltier temperature control platform maintained gels at 20°

C. throughout IEF. Focused gels were stored at −20° C. prior to sodium dodecyl sulfate-polyacrylamide gel electrophoresis (SDS-PAGE).

Example 4

Sodium Dodecyl Sulfate-Polyacrylamide Gel Electrophoresis

IEF strips were thawed and equilibrated in two steps prior to SDS-PAGE. First, strips were incubated for 10 minutes in equilibration buffer (50 mmol/L Tris-HCl, pH 8.8, 6 mol/L urea, 30% v/v glycerol, 2% w/v SDS) supplemented with 10 mg/mL DTT, followed by a 10 minute incubation in equilibration buffer supplemented with 25 mg/mL iodoacetamide. Then strips were rinsed once with SDS-PAGE buffer (25 mmol/L Tris, 192 mmol/L glycine, pH 8.3, 0.1% w/v SDS). Proteins were then resolved by 12.5% SDS-PAGE with IEF strips embedded in 5% stacking gel using a PROTEAN® II XL system (Bio-Rad, gel dimensions of 192×184×1 mm). Electrophoresis was carried out at 50 V for 30 minutes, followed by 150 V for 7.5 hours.

Example 5

Protein Transfer and Western Blotting

Following SDS-PAGE, gels were equilibrated in SDS-PAGE buffer supplemented to 20% v/v methanol for 10 minutes, then transferred to nitrocellulose (0.22 µm pore size, Osmonics Inc.) at 200 mA constant current for a period of 2 hours using a PROTEAN® TRANS-BLOT ® Cell (Bio-Rad). After transfer, nitrocellulose membranes were rinsed with phosphate-buffered saline/Tween-20 (PBS/T), consisting of (in mmol/L) NaCl 137, KCl 2.7, $Na_2HPO_4$ 10.1, $KH_2PO_4$ 1.8, pH 7.4 supplemented to 0.1% v/v Tween-20, then blocked overnight at 4° C. with 1% v/v blocking reagent (Roche Diagnostics) in PBS/T. Western blotting for MLC1 was carried out using a monoclonal antibody (mAb 39–121, provided by Spectral Diagnostics, Toronto, ON, Canada) at 1 µg/mL, and detected using alkaline-phosphatase conjugated anti-mouse IgG (Jackson ImmunoResearch Laboratories) and Renaissance CDP-STAR® western blot chemiluminescence reagent (NEN/Mandel) according to the manufacturer's protocol.

Example 6

Silver Staining of 2-DE Gels

2-DE gels were silver stained according to the protocol of Shevchenko et al. (Anal. Chem. 1996 68:850–858) which is a reversible staining method compatible with subsequent analysis of protein by mass spectrometry. In the procedure, gels were incubated overnight in 50% v/v methanol, 5% v/v acetic acid, followed by 50% v/v methanol for 10 minutes, then 10 minutes in deionized distilled (dd) $H_2O$. Gels were sensitized for 1 minute in 0.02% w/v sodium thiosulfate, followed by two 1-minute $ddH_2O$ washes, then incubated in prechilled (4° C.) 0.1% w/v silver nitrate for 20 minutes, followed again by two 1-minute $ddH_2O$ washes. Proteins were then visualized by several washes with developing solution (2% w/v sodium carbonate, 0.04% v/v formalin) until a desired level of staining was achieved, after which development was stopped with 5% v/v acetic acid.

Example 7

Image Analysis and Quantification

Silver-stained 2-DE gels were digitized at 150 dpi (pixels per inch) resolution using a POWERLOOKII® scanner (UMAX® Data Systems, Inc.) on a SUN® ULTRA5™ computer (Sun Microsystems, Inc.). Protein spots were then located, quantified, and matched to spots on other gels with the BioImage software INVESTIGATOR™ HT Proteome Analyzer 1.0.1 (Genomic Solutions, Inc.). Fifteen manually defined spots were selected as anchors for triangulation of remaining spots. Composite images were then prepared by matching spots from four gel images for each treatment group (adenosine and control), and normalized using a match ratio method to compensate for differences in protein loading and level of silver stain development between gels. Optimization of silver staining was required, as protein quantity and extent of staining time affects detection and quantification of proteins. Gels used for quantification were all within the optimal staining range for MLC1. Integrated intensities of the three MLC1 spots were summed to give an overall integrated intensity of MLC1 for each gel, then values were converted to percentages of the total MLC1 for each of the three spots. Thus, determination of the extent of phosphorylation (mean±standard error) was conducted within a single gel, and never between gels, in order to minimize differences that invariably arise when attempting to compare intensities between two silver-stained images. One way ANOVA was used to determine if a significant difference existed between experimental groups.

Example 8

Mass Spectrometry

Protein spots extracted from 2-DE gels were destained according to Gharahdaghi et al. (Electrophoresis 1999 20:601–605), then dried under vacuum before enzymatic digestion with sequence-grade modified trypsin (Promega). Tryptic peptides were extracted with 50% acetonitrile (ACN)/5% TFA, dried under vacuum, and reconstituted with 3 µL of 50% ACN/0.1% TFA. Reconstituted extract (0.5 µL) was then mixed with 0.5 µL of matrix (10 mg/mL α-cyano-4-hydroxy-trans-cinnamic acid in 50% ACN, 0.1% TFA), spotted on a stainless steel 100-well mass spectrometry plate, and air dried. Samples were analyzed using a VOYAGER® DE-Pro matrix-assisted laser desorption/ionization time-of-flight (MALDI-TOF) mass spectrometer (PerSeptive Biosystems) operated in the delayed extraction/reflector mode with an accelerating voltage of 20 kV, grid voltage of 72%, and a 50 nanosecond delay. Five spectra (50–100 laser shots/spectrum) were obtained for each sample. External calibration was performed using a Sequazyme Peptide Mass Standard kit (PerSeptive Biosystems) by spotting the following standards adjacent to the sample on the mass spectrometry plate: des-Arg-bradykinin, angiotensin-1, and Glu-fibrinopeptide B.

Example 9

Bioinformatic Data Analysis

Peptide mass fingerprinting was conducted with the database search tool MS-Fit in the program Protein Prospector (version 3.2.1), available at http://prospector.ucsf.edu/. A number of restrictions were applied to the initial search: species=mammals, pI range=4–7, mass range=0–30 kDa (1 Da mass tolerance), with a minimum of 4 peptides to match, and a maximum of one missed tryptic cleavage. Top candidate proteins identified by MS-Fit were then analyzed for theoretical tryptic peptide fragments using MS-Digest, taking into account phosphorylation of Ser, Thr, and Tyr residues, then compared to the observed spectra, allowing a mass tolerance of 0.2 Da. MLC1 sequence alignments were prepared with the program Clustal W (version 1.81) provided online by the European Bioinformatics Institute at http://www2.ebi.ac.uk/clustalw/.

Example 10

MLC1 Phosphorylation in Acute Versus Chronic Myocardial Damage

Model A: Ischemia Induced Failing Heart Model in Swine (Complete Occlusion and Chronic (Analyzed 6 Weeks after Surgery))

Neutered male swine (13–34.0 kg) underwent open chest surgery for occlusion of the mid-third of the left anterior descending branch of coronary artery (LAD) to induce heart failure. Sham-operated swine (SHAM) or controls underwent the same surgical procedure except the LAD was not occluded. During open chest surgery and at termination, animals were under general anesthesia (a preanaesthetic, atropine followed by a combination of ketamine, midazolam and isoflurane, with anesthesia maintained by isoflurane) Upon recovery the animals received analgesics as needed. At 4 weeks, echocardiography was performed on conscious mildly sedated animals. To estimate the left ventricle ejection fraction echocardiographs were performed in the lateral position, left side of the swine down, using a PieMedical 200 scanner equipped with a 5.0/7.5 MHz probe. At 6 weeks post-surgery animals were sacrificed, the hearts were excised, immediately snap-frozen in liquid nitrogen and stored at −80° C. All experimental procedures conformed to guidelines of the Canadian Council of Animal care and were approved by Queen's University Animal Care Committee. Model B—Ischemic Induced Stunning in Swine (Low Flow Done on Conscious Animals Acute for 60 Minutes with about 40% Blood Flow)

A left thoracotomy was performed in domestic swine (weight, 22–25 kg), and the pigs were instrumented to measure global and regional myocardial function in accordance with procedures described by Kudej et al. (Circ. Res. 1998 82:1199–2050 and Shen et al. (Circ. Res. 1995 76:479–88). After 1 week of post-operative recovery, myocardial stunning was induced by introducing air into the hydraulic occluder to reduce coronary blood flow by approximately 40% for 90 minutes and followed by 60 minutes full reperfusion. Stunned tissue was taken from a region within ischemic zone. Control tissue was taken from a region remote from the ischemic zone in same animal. SDS PAGE and 2-DE Heart tissue from a non-infarcted region of the left ventricle was homogenized in 20 mM Tris (pH 6.8) and 0.2 mM sodium vanidate, 50 mM sodium fluoride, 2 mM EDTA, 1 $\mu$M leupeptin, 1 $\mu$M pepstatin A, 0.36 $\mu$M aprotinin, 0.25 mM phenylmethylsulfonyl fluoride at 4° C. at a ratio of tissue weight:buffer volume equal to 1:4 (whole tissue homogenate). 2-DE was carried out as described herein. 100 $\mu$g of either the cytoplasmic or myofilament protein enriched extracts obtained using the IN SEQUENCE extraction method described in Example 2, were diluted in 500 $\mu$l of 8 M urea, 2.5 M thiourea, 4% CHAPS (w/v), 0.5% pH 3.5–10 ampholyte (v/v) (Sigma, St. Louis, Mo., USA), 0.01% bromophenol blue (w/v). Samples were loaded on a pH 3–10 immobilized linear gradient IPG Strips (170 mm) and isoelectric focusing performed using a Protean IEF cell system (Bio-Rad, Hercules, Calif., USA). Gels were actively rehydrated at 50 V for 10 hours, then rapid voltage ramping, limited by maximum current of 50 $\mu$A per gel, was applied in steps at 100 V (25 Vh), 500 V (125 Vh), 1000 V (250 Vh) and 8000 V to accumulate 65 kVh. In the second dimension proteins from the strips were resolved on 12% SDS PAGE gels using a Protean II XL system (Bio-Rad, Hercules, Calif., USA)(192 mm×184 mm×1 mm). For regular SDS PAGE (12.5%) a mini-Protean II system (Bio-Rad, Hercules, Calif., USA)(75 mm×100 mm) was used. Gels were either silver or Coomassie Blue stained. When required, gels were transferred to nitrocellulose (NitroPure nitrocellulose from Osmonics Inc., Westborough, Mass., USA) and western blot analysis was carried out. Primary antibody was anti-myosin light chain 1 at 1 $\mu$g/ml; secondary antibody were alkaline-phosphatase conjugated anti-mouse IgG (ImmunoResearch Laboratory, West Grove, Pa., USA), at 1/10,000 dilution (stock concentration 0.3 mg/ml); detection by Immun-Star chemiluminescence system (BioRad, Hercules, Calif., USA).

What is claimed is:

1. A method for identifying an agent which inhibits damage to cardiac and skeletal muscle comprising:
   (a) combining adenosine triphosphate and a test agent with purified myosin, myosin light chain 1 (MLC1) or isoform thereof, or myofilament or skinned muscle fiber in the presence of an enzyme that modulates phosphorylation of MLC1; and
   (b) monitoring phosphorylation of MLC1 in the purified myosin, myosin light chain 1 (MLC1) or isoform thereof, or myofilament or skinned muscle fiber in the presence and absence of the test agent, wherein an increase in MLC1 phosphorylation in the purified myosin, myosin light chain 1 (MLC1) or isoform thereof, or myofilament or skinned muscle fiber in the presence of the test agent is indicative of the test agent inhibiting damage to cardiac and skeletal muscle.

2. The method of claim 1 wherein the myosin, myosin light chain 1, or isoform thereof are obtained from a biological sample using IN Sequence extraction.

3. The method of claim 1 wherein MLC1 phosphorylation is increased by increasing activity of a phosphatase that acts on MLC1 phosphorylation.

4. The method of claim 1 wherein MLC1 phosphorylation is increased by increasing activity of a kinase that acts on MLC1 phosphorylation.

5. The method of claim 1 wherein the increased MLC1 phosphorylation occurs at one or more of residues Thr64, Ser194 and Ser195 of human MLC1.

6. The method of claim 1 wherein the increased MLC1 phosphorylation occurs at one or more of residues Thr69 and Ser200 of rat MLC1.

7. The method of claim 1 wherein the identified agent protects against muscle damage caused by a cardiomyopathy, hypertension, or a free radical.

8. The method of claim 1 wherein the identified agent protects against muscle damage caused by ischemia, hypoxia, or ischemia/hypoxia with reperfusion.

9. The method of claim 1 wherein the ability of the agent to increase MLC1 phosphorylation is assessed in vitro in myofilament or skinned muscle fibers.

10. A method for identifying an agent which inhibits damage to cardiac and skeletal muscle comprising:
    (a) combining a test agent with isolated myocytes isolated whole hearts or whole hearts or vivo; and
    (b) monitoring phosphorylation of MLC1 in the isolated myocytes or whole hearts in the presence and absence of the test agent, wherein an increase in MLC1 phosphorylation in the isolated myocytes or whole hearts in the presence of the test agent is indicative of the test agent inhibiting damage to cardiac and skeletal muscle.

11. The method of claim 10 wherein MLC1 phosphorylation is increased by decreasing activity of a phosphatase that acts on MLC1 phosphorylation.

12. The method of claim 10 wherein MLC1 phosphorylation is increased by increasing activity of a kinase that acts on MLC1 phosphorylation.

13. The method of claim 10 wherein the increased MLC1 phosphorylation occurs at one or more of residues Thr64, Ser194 and Ser195 of human MLC1.

14. The method of claim 10 wherein the increased MLC1 phosphorylation occurs at one or more of residues Thr69 and Ser 200 of rat MLC1.

15. The method of claim 10 wherein the identified agent protects against muscle damage caused by a cardiomyopathy, hypertension, or a free radical.

16. The method of claim 10 wherein the identified agent protects against muscle damage caused by ischemia, hypoxia, or ischemia/hypoxia with reperfusion.

17. A method for identifying an enzyme as a therapeutic target for agents which inhibit damage to cardiac and skeletal muscle comprising:
(a) combining an enzyme with purified myosin, myosin light chain 1 (MLC1) an isoform thereof, or myofilament or skinned muscle fiber in the presence of adenosine triphosphate; and
(b) monitoring phosphorylation of MLC1 in the purified myosin, myosin light chain 1 (MLC1) or isoform thereof, or myofilament or skinned muscle fiber in the presence and absence of the enzyme, wherein modulation of MLC1 phosphorylation status in the presence of the enzyme is indicative of the enzyme being a therapeutic target for an agent which inhibits damage to cardiac or skeletal muscle.

18. The method of claim 17 wherein the myosin, myosin light chain 1, or isoform thereof are obtained from a biological sample using IN Sequence extraction.

19. The method of claim 17 wherein the enzyme is a phosphatase and decreasing activity of the phosphatase increases MLC1 phosphorylation.

20. The method of claim 17 wherein the enzyme is a kinase and increasing activity of the kinase increases MLC1 phosphorylation.

21. The method of claim 17 wherein MLC1 phosphorylation is increased at one or more of residues Thr64, Ser194 and Ser195 of human MLC1.

22. The method of claim 17 wherein MLC1 phosphorylation is increased at one or more of residues Thr69 and Ser200 of rat MLC1.

* * * * *

UNITED STATES PATENT AND TRADEMARK OFFICE
CERTIFICATE OF CORRECTION

PATENT NO. : 6,790,634 B2
DATED : September 14, 2004
INVENTOR(S) : Van Eyk et al.

It is certified that error appears in the above-identified patent and that said Letters Patent is hereby corrected as shown below:

Column 14,
Line 35, please delete "increasing" and insert -- decreasing --.
Line 57, please delete "myocytes isolated" and insert -- myocytes, isolated --.

Column 15,
Line 20, please delete "an" and insert -- or --.

Signed and Sealed this

First Day of February, 2005

JON W. DUDAS
*Director of the United States Patent and Trademark Office*